(12) United States Patent
Shang

(10) Patent No.: US 9,095,488 B2
(45) Date of Patent: Aug. 4, 2015

(54) DEVICE FOR DRIVING LIFTING MOVEMENT OF EXAMINATION BED, EXAMINATION BED, AND MEDICAL EQUIPMENT

(75) Inventor: Hong Shang, Shanghai (CN)

(73) Assignee: Siemens Aktiengesellschaft, München (DE)

( * ) Notice: Subject to any disclaimer, the term of this patent is extended or adjusted under 35 U.S.C. 154(b) by 112 days.

(21) Appl. No.: 13/543,348

(22) Filed: Jul. 6, 2012

(65) Prior Publication Data

US 2013/0174341 A1    Jul. 11, 2013

(30) Foreign Application Priority Data

Jul. 7, 2011   (CN) ...................... 2011 2 0237776 U

(51) Int. Cl.
  *A61G 13/06*    (2006.01)
  *A61B 6/04*    (2006.01)
  *A61B 5/055*    (2006.01)
  *A61B 6/03*    (2006.01)

(52) U.S. Cl.
  CPC .............. *A61G 13/06* (2013.01); *A61B 5/0555* (2013.01); *A61B 6/0407* (2013.01); *A61B 6/032* (2013.01)

(58) Field of Classification Search
  CPC .... A61B 6/032; A61B 6/0407; A61B 6/0555; A61G 13/06

USPC .............................................. 5/601, 611, 600
See application file for complete search history.

(56) References Cited

U.S. PATENT DOCUMENTS

2006/0016008 A1*   1/2006  Choi et al. ........................ 5/611
2010/0325797 A1*  12/2010  Horne ................................ 5/611
2012/0198624 A1*   8/2012  Zheng et al. ...................... 5/601

FOREIGN PATENT DOCUMENTS

WO        WO 9111979 A1  *  8/1991

* cited by examiner

*Primary Examiner* — Peter M Cuomo
*Assistant Examiner* — Brittany Wilson
(74) *Attorney, Agent, or Firm* — Lempia Summerfield Katz LLC

(57) ABSTRACT

A device for driving the lifting movement of an examination bed includes a horizontal support frame and a base support component that is pivotally connected to a swing arm component. The device includes a swing bar component including a swing bar. A first end of the swing bar is connected to a lifting movement element, and a second end of the swing bar is connected to a set position of the swing arm component. The device includes a sliding component including a linear guide element and at least one sliding element slidable relative to the linear guide element. The device also includes a swing arm component including at least one swing arm, with the first end of each of the swing arms being connected to the base support component and the second end of each of the swing arms being connected to the sliding element.

13 Claims, 3 Drawing Sheets

DEVICE FOR DRIVING LIFTING MOVEMENT OF EXAMINATION BED, EXAMINATION BED, AND MEDICAL EQUIPMENT

This application claims the benefit of CN 201120237776.7, filed on Jul. 7, 2011.

TECHNICAL FIELD

The present embodiments relate to the technical field of a device for driving the lifting movement of an examination bed.

BACKGROUND

In Magnetic Resonance Imaging (MRI) equipment, computerized tomography (CT) equipment and other medical equipment, the examination bed for bearing patients may use lifting movement so as to move the patient to an effective diagnosis height and into an effective diagnosis area by a horizontal feeding mechanism for diagnosis.

FIG. 1 shows a lead screw nut type driving device for an MRI equipment hospital bed in the prior art. As shown in FIG. 1, the lead screw nut type driving device is located outside an examination bed 20. During the use, a motor 60 drives a lead screw 50 to rotate using a belt, so that a lead screw nut 40 sleeved on the lead screw 50 moves upward or downward, while the lead screw nut 40 is fixedly connected to the examination bed 20 via a vertical support component 30. The lead screw nut type driving device may drive the examination bed 20 to make the lifting movement. As a result, the examination bed 20 may be moved to the effective diagnosis height and further moved into the effective diagnosis area of a magnet 10 using a horizontal feed mechanism. The lead screw nut type driving device occupies a large space beside the hospital bed, so the operation of the operator is inconvenient. Due to such a horizontally placed installation structure, the lead screw suffers from significant horizontal stress and is in a superposition state. This brings a great deal of difficulty to the installation and also brings high cost.

SUMMARY AND DESCRIPTION

The present embodiments may obviate one or more of the drawbacks or limitations in the related art. For example, an improved device for driving the lifting movement of an examination bed is provided.

In one embodiment, the device for driving the lifting movement of an examination bed includes a base support component, a vertical lifting component, a swing bar component, a swing arm component, a sliding component, and a horizontal support frame for bearing a bed plate. The base support component includes a first support member for positioning the vertical lifting component and a second support member pivotally connected to the swing arm component. The vertical lifting component includes a lifting drive element and a lifting movement element to be used in cooperation with the lifting drive element. The lifting movement element has, in a vertical plane, a connecting end that is pivotally connected to the swing bar component. The swing bar component includes at least one swing bar. The first end of the swing bar is connected to the connecting end of the lifting movement element via a rotary shaft, and the second end of the swing bar is connected to a connecting end at a set position of the swing arm component via a rotary shaft. The sliding component includes a linear guide element fixed in the longitudinal direction under the horizontal support frame and at least one sliding element slidable relative to the linear guide element. The sliding element has a connecting end that is pivotally connected to the swing arm component. The swing arm component includes at least one swing arm. The first end of the swing arm is connected to the second support member via a rotary shaft. The second end of the swing arm is connected to the connecting end of the sliding element via a rotary shaft. The swing arm has, at a set position in the middle of the swing arm in the longitudinal direction, a connecting end that is pivotally connected to the second end of the swing bar.

In one embodiment, the device further includes a synchronous transmission component, and the lifting drive element receives the drive of a driving motor via the synchronous transmission component.

In another embodiment, the device further includes a driving motor for driving the lifting drive element to rotate.

In one embodiment, the lifting drive element is a lead screw. The lifting movement element is a lead screw nut, and the first support member sets the lead screw in terms of position. Alternatively, the lifting drive element is a chain wheel, and the lifting movement element is a chain or push chain. The first support member sets the chain or push chain in terms of direction.

In yet another embodiment, in the case that the lifting movement element is a lead screw nut, the device further includes a safety nut used in cooperation with the lead screw nut.

In one embodiment, the linear guide element is a guide rail, and the sliding element is a sliding seat slidable along the guide rail. Alternatively, the linear guide element is a sliding groove, and the sliding element is a sliding block slidable along the sliding groove.

In another embodiment, the device includes a retractable vertical orientation post connected between the base support component and the horizontal support frame.

In one embodiment, the device further includes a base located under the base support component for securing the base support component.

In yet another embodiment, the device further includes castors fitted on the base.

One embodiment of an examination bed includes a device for driving the lifting movement of an examination bed according to any specific implementation described above.

In another embodiment, medical equipment includes an examination bed described above.

As the conventional design concept is changed in the present embodiments, the swing bar and the swing arm are driven to unfold and fold by the vertical lifting movement of the lifting movement element (e.g., lead screw nut), so that the horizontal support frame slidingly connected to the swing arm rises and falls, and the lifting of the bed plate on the horizontal support frame is realized. As such, a structure is relatively simple, the installation is convenient, and the cost is low. In addition, such a structure may also realize a relatively low working position and a relatively large lifting range.

For the vertical lifting component formed of a lead screw and a lead screw nut, by additionally installing one safety nut for the lead screw nut, the examination bed may be protected from emergencies such as, for example, sudden sinking of the bed plate caused by the wear of the lead screw nut.

By providing a retractable vertical orientation post between the base support component and the horizontal support frame, the horizontal support frame may be kept in horizontal vertical lifting.

In addition, by providing a base and castors for the examination bed, the examination bed may be moved conveniently.

DETAILED DESCRIPTION OF THE DRAWINGS

With a device for driving the lifting movement of an examination bed with convenient installation and relatively low cost, the conventional design concept is changed. In one embodiment, a swing bar and a swing arm are driven to unfold and fold by a vertical lifting movement of a lifting movement element (e.g., a lead screw nut), so that a horizontal support frame slidingly connected to the swing arm makes a lifting movement, and the lifting of a bed plate on the horizontal support frame is realized.

In order to make the object, technical solutions and advantages of the present embodiments more apparent, the present embodiments are further described in detail hereinbelow.

Figure 1:
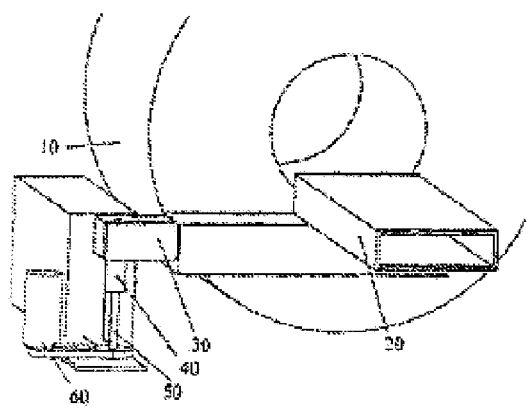
FIG. 1 is a lead screw nut type driving device for an MRI equipment hospital bed in the prior art.
Figure 2A:
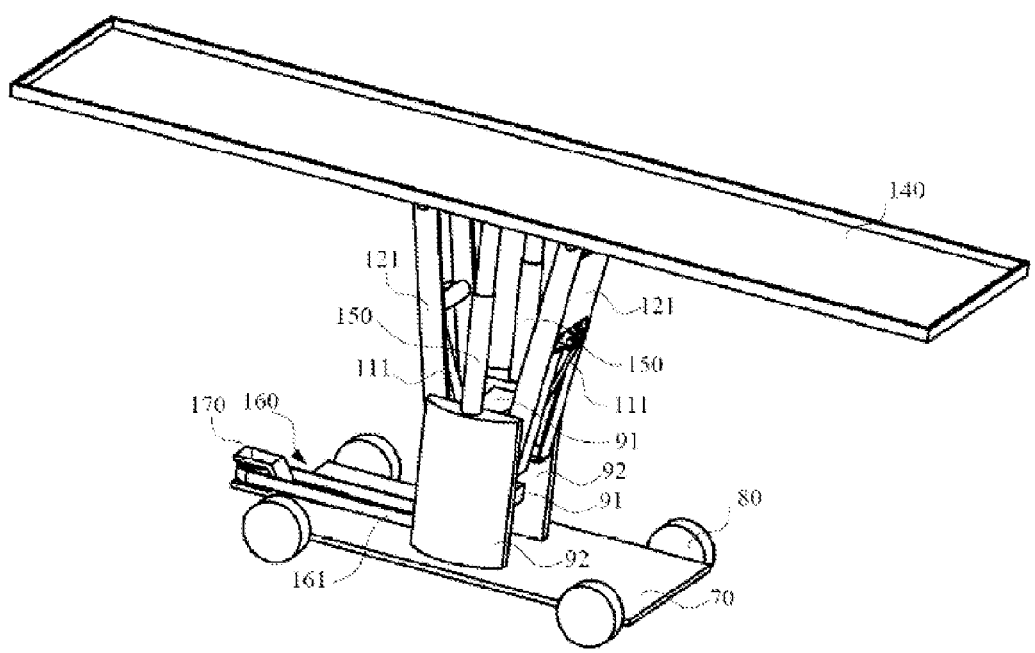
FIGS. 2a-2c are exemplary structure diagrams of a device for driving the lifting movement of an examination bed in a folded state.
Figure 2B:
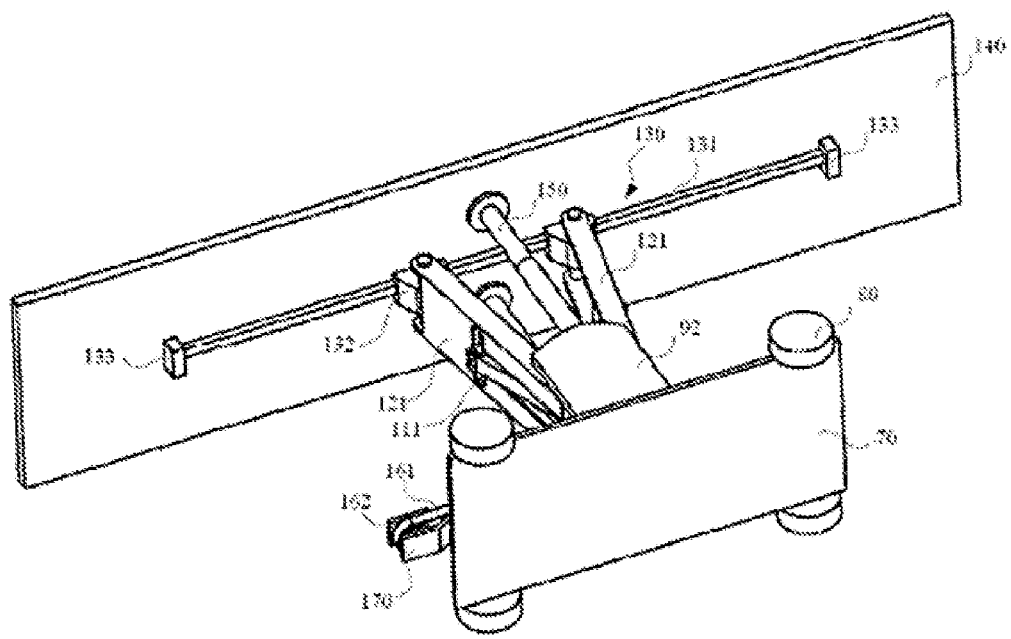
Figure 2C:
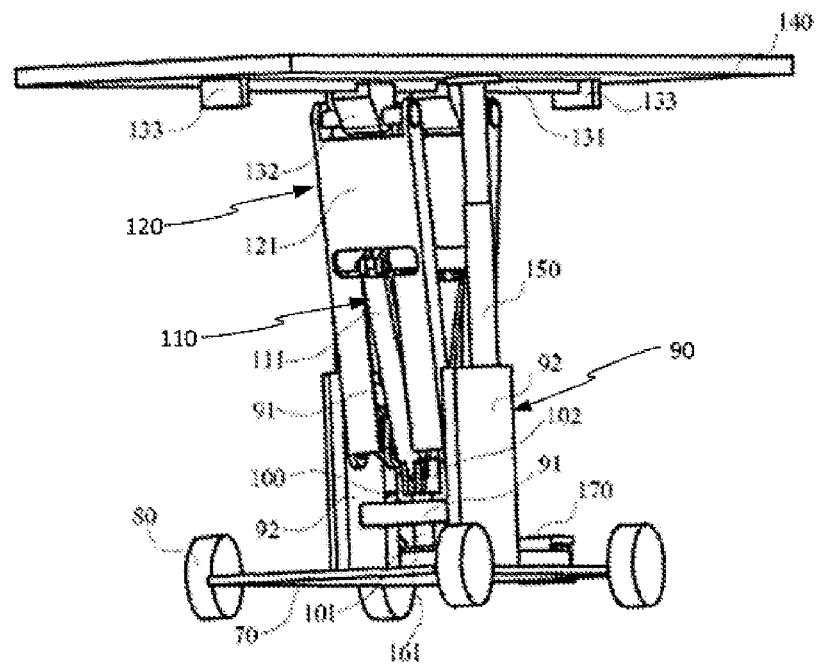
Figure 3:
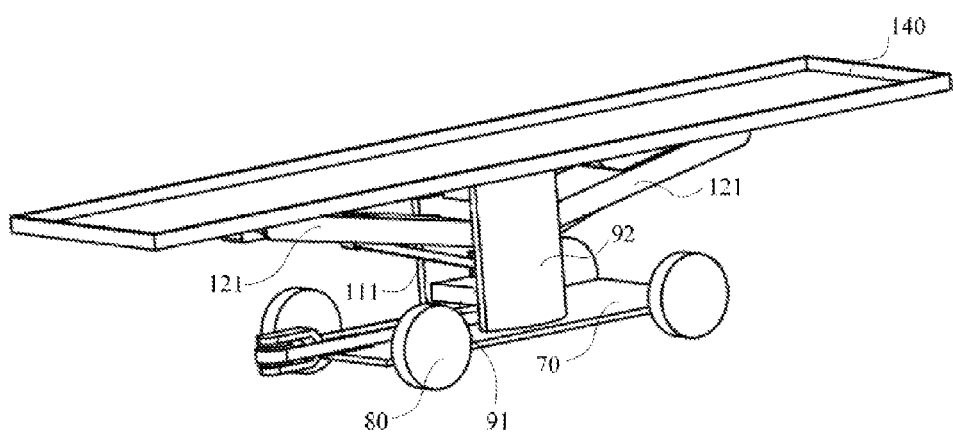
FIG. 3 is an exemplary structure diagram of a device for driving the lifting movement of an examination bed in an unfolded state.

FIGS. 2a-2c are exemplary structure diagrams of a device for driving the lifting movement of an examination bed in a folded state. FIGS. 2a-2c are corresponding accompanying drawings of the device in different visual angles for displaying each part of the device clearly. FIG. 3 is an exemplary structure diagram of a device for driving the lifting movement of an examination bed in an unfolded state. In the present description, the device for driving the lifting movement of an examination bed are described in detail mainly according to the orientation shown in FIG. 2a; unless specifically noted, the upper, lower, left, right, front, back, vertical and horizontal orientations involved in the present description are all in terms of the visual angle shown in FIG. 2a for the sake of easy explanation.

With reference to FIGS. 2a-2c and FIG. 3, the device for driving the lifting movement of the examination bed includes a base 70, castors 80 installed on the base 70, a base support component 90, a vertical lifting component 100, a swing bar component 110, a swing arm component 120, a sliding component 130, a horizontal support frame 140 for bearing a bed plate, a retractable orientation post 150, a synchronous belt transmission component 160, and a belt wheel bracket 170.

In this embodiment, four castors 80 are installed on the base 70, so that the examination bed may be moved freely. For an examination bed not to be moved, no castor 80 may be installed on the base 70. Additionally, in some cases, the base 70 may also be omitted, and the base support component 90 is directly placed on the ground.

The base support component 90 includes a first support member 91 for positioning the vertical lifting component 100 and a second support member 92 pivotally connected to the swing arm component 120. In this embodiment, the second support member 92 includes two uprightly placed support beams for enhancing the strength. The support beams in this embodiment are in a structure of curved columns. The first support member 91 includes upper and lower support frames horizontally fixed between the two uprightly placed support beams, and the first support member 91 and the second support member 92 form a right-angle trapezoid structure together. In this embodiment, the lower end of the second support member 92 is fixed on the base 70, and the middle part of the second support member 92 is provided with an installation hole for being pivotally connected to the swing arm component 120 at a position near an outer side in the horizontal direction. In other embodiments, the first support member 91 and the second support member 92 may also be elements in other structure forms, and both the first support member 91 and the second support member 92 may also be the same element. The particular implementation may be determined according to practical requirements, which is not limited in the present application.

The vertical lifting component 100 includes a lifting drive element 101 and a lifting movement element 102 to be used in cooperation with the lifting drive element 101. The lifting movement element 102 has, in a vertical plane, a connecting end that is pivotally connected to the swing bar component 110. For example, the connecting end may be an earring seat fixed on the lifting movement element 102. In this implementation, the lifting drive element 101 is a lead screw. Correspondingly, the lifting movement element 102 is a lead screw nut mated with the lead screw. The first support member 91 may set the lead screw using the upper and lower horizontal support frames in terms of position.

According to another embodiment, the lifting drive element 101 may also be a chain wheel. Correspondingly, the lifting movement element 102 is a chain or push chain mated with the lifting drive element 101. The first support member 91 may set the chain or push chain in terms of direction (e.g., guiding the chain or push chain).

In order to improve the safety of the examination bed, in this embodiment, one safety nut (not shown in the figure) may be additionally installed for the lead screw nut, for protecting the examination bed from emergencies such as sudden sinking of the bed plate caused by the wear of the lead screw nut when the lead screw nut is worn.

In addition, according to different implementations, the lifting drive element 101 may be driven by an external driving motor (not shown in the figure), or the device may also further include one driving motor (not shown in the figure) (e.g., having an internal driving motor). The lifting drive element 101 may be driven by this internal driving motor. In the embodiments shown in FIGS. 2a-3, the case that an external driving motor is used is taken as example. The present embodiment does not place any restriction on the specific mode of implementation employed in other application scenarios.

The driving motor may be directly connected to the lifting drive element 101 to directly drive the lifting drive element 101 to rotate. A synchronous transmission component 160 may also be further provided between the driving motor and the lifting drive element 101, according to practical requirements, so that the lifting drive element 101 is driven by the synchronous transmission component 160 to rotate. In the embodiments shown in FIGS. 2a-3, an embodiment where the device includes a synchronous belt transmission component including a belt 161 and a belt wheel 162 is provided as an example. The driving motor drives the lifting drive element 101 using the synchronous belt transmission component. In different implementations, the synchronous transmission component may also be a synchronous chain transmission component including, for example, a chain wheel and a chain, and there is no need to enumerate all the possibilities. In the embodiments shown in FIGS. 2a-3, the belt wheel 162 for connecting to the motor is installed on a belt wheel bracket 170, and the belt wheel bracket 170 may be directly connected to the driving motor.

The swing bar component 110 includes at least one swing bar 111. In this embodiment, the swing bar component includes two swing bars 111, for example. The two swing bars 111 are oppositely arranged on either side of the vertical lifting component 100, and the swing track thereof is parallel to the two upright support beams. The first end of each of the swing bars 111 is connected to the connecting end 103 of the lifting movement element 102 via a rotary shaft. The second end of the swing bar 111 is connected to a connecting end at a set position of the swing arm component 120 via a rotary shaft.

The sliding component 130 includes a linear guide element 131 fixed in the longitudinal direction under the horizontal support frame 140 and at least one sliding element 132 slidable relative to the linear guide element 131 (e.g., one linear guide element 131 and two sliding elements 132). The two ends of the linear guide element 131 have stop blocks 133 for stopping the sliding elements 132, and the sliding elements 132 have a connecting end that is pivotally connected to the swing arm component 120. In this embodiment, the linear guide element 131 is a guide rail, and correspondingly, the sliding elements 132 are sliding seats slidable along the guide rail. The linear guide element 131 may also be a sliding groove, and correspondingly, the sliding element 132 may be a sliding block slidable along the sliding groove. The particular implementation to be employed may be determined according to practical requirements. As the movement distance of the lifting movement element 102 (e.g., the lead screw nut in the figures) may have stops, the two ends of the linear guide element 131 may not provide stop blocks 133 for stopping the sliding element 132.

According to different application scenarios, two or more parallel linear guide elements 131 may also be provided, and correspondingly, there is at least one sliding element 132 mated with each linear guide element 131 (e.g., two sliding elements 132).

The swing arm component 120 includes at least one swing arm 121 (e.g., two swing arms 121). The two swing arms 121 are oppositely fitted on either side of the vertical lifting component 100, and the swing track thereof is parallel to the two upright support beams. In this embodiment, in order to enhance the strength of the swing arms 121, each of the swing arms 121 may be set in a groove structure, and the two ends of the swing arms 121 may be set in a structure of earring seats. The first end of the swing arm 121 may be connected to the two upright support beams of the second support member 92 via rotary shafts, the second end of the swing arm 121 may be connected to the connecting end of the sliding element 132 via a rotary shaft, and the swing arm 121 has, at a set position in the middle of the swing arm 121 in the longitudinal direction, a connecting end that is pivotally connected to the second end of the swing bar 111. For example, the connecting end may be as follows: a cylinder connected between two folded edges of the groove structure is fixed at the set position, and an earring seat is fixed on the cylinder. In this embodiment, in order to avoid getting in the way of the swing track of the swing bars 111, one opening is provided at the first end of the swing arm 121, and the length of the opening is avoided getting in the way of the swing track of the swing bar 111.

In a case that there are two or more linear guide elements 131 and a plurality of sliding elements 132 mated with each of the linear guide elements 131, the number of the swing arms 121 may also be adjusted correspondingly. In one embodiment, the number of the swing arms 121 may be consistent with the number of the sliding elements 132 (e.g., it is better to provide that one swing arm 121 is connected to one sliding element 132).

In one embodiment, there are two parallel linear guide elements 131, four sliding elements 132 and four swing arms 121. Each of the swing arms 121 may be set in a bar structure, and the first end of each of the swing arms 121 is connected to one upright support beam via a rotary shaft. The second end of each of the swing arms 121 is connected to one sliding element 132. In one embodiment, two swing bars 111 may be provided, and each of the swing bars is respectively connected to the connecting end at a set position in the middle of two swing arms 121. In another embodiment, four swing bars may be provided, and each of the swing bars is respectively connected to the connecting end at a set position in the middle of one swing arm 121. The particular implementation to be employed may be determined according to practical requirements, and there is no need to enumerate all the possibilities.

In order to provide that the horizontal support frame 140 may be kept horizontal during vertical lifting, in this embodiment, a retractable vertical orientation post 150 may be further provided between the base support component 90 and the horizontal support frame 140. One end of the orientation post 150 is connected to the upright support beams, and the other end of the orientation post 150 is connected to the horizontal support frame 140.

When the examination bed is to be lifted up, the driving motor drives the lifting drive element 101 (e.g., the lead screw in the figure) to rotate in a first direction. The lifting movement element 102 (e.g., the lead screw nut on the lead screw) moves downward to drive the swing bar 111 connected to the lifting movement element 102 to swing inward and downward, so as to push the swing arm 121 connected to the swing bar 111 to swing inward. The swing arm 121 drives the sliding element 132 to slide towards the center of the horizontal support frame 140, and at the same time, the horizontal support frame 140 is pushed upward, and the horizontal support frame 140 is kept to lift up horizontally under the action of the orientation post 150. By way of the downward traction of the lifting movement element 102, the swing bar 111 and the swing arm 121 are driven to fold, so as to lift the horizontal support frame 140 up.

When the examination bed is to be lowered, the driving motor drives the lifting drive element 101 (e.g., the lead screw in the figure) to rotate in a second direction opposite to the first direction. The lifting movement element 102 (e.g., the lead screw nut on the lead screw) moves upward to drive the swing bar 111 connected to the lifting movement element 102 to swing outward and upward, so as to push the swing arm 121 connected to the swing bar 111 to swing outward. The swing arm 121 drives the sliding element 132 to slide towards the edge of the horizontal support frame 140, and at the same time, the horizontal support frame 140 is pulled downward, and the horizontal support frame 140 is kept to lift down horizontally under the action of the orientation post 150. By way of the upward traction of the lifting movement element 102, the swing bar 111 and the swing arm 121 are driven to unfold, so as to lift the horizontal support frame 140 down.

The above contents describe the device for driving the lifting movement of an examination bed in detail. The examination bed in the present embodiments may include a lifting movement driving device in any one of the above specific implementations. The medical equipment in the present embodiments may include the examination bed including a lifting movement driving device in any one of the above specific implementations. The medical equipment may be MRI equipment, CT equipment, or other medical equipment.

The present embodiments realize the lifting of the bed plate on the horizontal support frame. As such structure is relatively simple, the installation is convenient, and the cost is low. In addition, such structure may also realize relatively low working position and relatively large lifting range.

What are described above are embodiments of the invention and are not to limit the present invention. Any modifications, equivalents, or improvements within the spirit and principle of the present embodiments are covered.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for driving a lifting movement of an examination bed, the device comprising:
   a base support component;
   a vertical lifting component;
   a swing bar component;
   a swing arm component;
   a sliding component;
   a horizontal support frame for bearing a bed plate; and
   a retractable vertical orientation post connected between the base support component and the horizontal support frame,
   wherein the base support component comprises a first support member for positioning the vertical lifting component and a second support member pivotally connected to the swing arm component,
   wherein the vertical lifting component comprises a lifting drive element and a lifting movement element to be used in cooperation with the lifting drive element, the lifting movement element having, in a vertical plane, a connecting end pivotally connected to the swing bar component,
   wherein the swing bar component comprises at least one swing bar, a first end of the at least one swing bar being connected to the connecting end of the lifting movement element via a first rotary shaft and a second end of the at least one swing bar being connected to a connecting end at a set position of the swing arm component via a second rotary shaft,
   wherein the sliding component comprises a linear guide element fixed in a longitudinal direction under the horizontal support frame, and at least one sliding element slidable relative to the linear guide element, the at least one sliding element having a connecting end pivotally connected to the swing arm component, and
   wherein the swing arm component comprises at least one swing arm, a first end of the at least one swing arm being connected to the second support member via a third rotary shaft, a second end of the at least one swing arm being connected to the connecting end of the at least one sliding element via a fourth rotary shaft, the swing arm having, at a set position in the middle of the swing arm in the longitudinal direction, a connecting end that is pivotally connected to the second end of the at least one swing bar.

2. The device according to claim 1, further comprising a synchronous transmission component,
   wherein the lifting drive element is operable to receive a drive of a driving motor via the synchronous transmission component.

3. The device according to claim 1, wherein the lifting drive element is a lead screw, the lifting movement element is a lead screw nut, and the first support member sets the lead screw in terms of position, or
   wherein the lifting drive element is a chain wheel, the lifting movement element is a chain or a push chain, and the first support member sets the chain or push chain in terms of direction.

4. The device according to claim 3, wherein the lifting movement element is the lead screw nut, and
   wherein the device further comprises a safety nut used in cooperation with the lead screw nut.

5. The device according to claim 1, wherein the linear guide element is a guide rail, and the at least one sliding element is a sliding seat slidable along the guide rail, or
   wherein the linear guide element is a sliding groove, and the at least one sliding element is a sliding block slidable along the sliding groove.

6. The device according to claim 1, further comprising a base located under the base support component for securing the base support component.

7. The device according to claim 2, further comprising a base located under the base support component for securing the base support component.

8. The device according to claim 3, further comprising a base located under the base support component for securing the base support component.

9. The device according to claim 4, further comprising a base located under the base support component for securing the base support component.

10. The device according to claim 5, further comprising a base located under the base support component for securing the base support component.

11. The device according to claim 6, further comprising castors fitted on the base.

12. An examination bed comprising:
    a device for driving the lifting movement of the examination bed, the device comprising:
       a base support component;
       a vertical lifting component;
       a swing bar component;
       a swing arm component;
       a sliding component;
       a horizontal support frame for bearing a bed plate; and
       a rectangle vertical orientation post connected between the base support component and the horizontal support frame,
    wherein the base support component comprises a first support member for positioning the vertical lifting component and a second support member pivotally connected to the swing arm component,
    wherein the vertical lifting component comprises a lifting drive element and a lifting movement element to be used in cooperation with the lifting drive element, the lifting movement element having, in a vertical plane, a connecting end pivotally connected to the swing bar component,
    wherein the swing bar component comprises at least one swing bar, a first end of the at least one swing bar being connected to the connecting end of the lifting movement element via a first rotary shaft and a second end of the at least one swing bar being connected to a connecting end at a set position of the swing arm component via a second rotary shaft,
    wherein the sliding component comprises a linear guide element fixed in a longitudinal direction under the horizontal support frame, and at least one sliding element slidable relative to the linear guide element, the at least one sliding element having a connecting end pivotally connected to the swing arm component, and wherein the swing arm component comprises at least one swing arm, a first end of the at least one swing arm being connected to the second support member via a third rotary shaft, a second end of the at least one swing arm being connected to the connecting end of the at least one sliding element via a fourth rotary shaft, the swing arm having, at a set position in the middle of the swing arm in the longitudinal direction, a connecting end that is pivotally connected to the second end of the at least one swing bar.

13. Medical equipment comprising:

an examination bed comprising:
- a device for driving the lifting movement of the examination bed, the device comprising:
  - a base support component;
  - a vertical lifting component;
  - a swing bar component;
  - a swing arm component;
  - a sliding component;
  - a horizontal support frame for bearing a bed plate; and
  - a retractable vertical orientation post connected between the base support component and the horizontal support frame, wherein the base support component comprises a first support member for positioning the vertical lifting component and a second support member pivotally connected to the swing arm component, wherein the vertical lifting component comprises a lifting drive element and a lifting movement element to be used in cooperation with the lifting drive element, the lifting movement element having, in a vertical plane, a connecting end pivotally connected to the swing bar component, wherein the swing bar component comprises at least one swing bar, a first end of the at least one swing bar being connected to the connecting end of the lifting movement element via a first rotary shaft and a second end of the at least one swing bar being connected to a connecting end at a set position of the swing arm component via a second rotary shaft, wherein the sliding component comprises a linear guide element fixed in a longitudinal direction under the horizontal support frame, and at least one sliding element slidable relative to the linear guide element, the at least one sliding element having a connecting end pivotally connected to the swing arm component, and wherein the swing arm component comprises at least one swing arm, a first end of the at least one swing arm being connected to the second support member via a third rotary shaft, a second end of the at least one swing arm being connected to the connecting end of the at least one sliding element via a fourth rotary shaft, the swing arm having, at a set position in the middle of the swing arm in the longitudinal direction, a connecting end that is pivotally connected to the second end of the at least one swing bar.

\* \* \* \* \*